United States Patent [19]

Deschler et al.

[11] Patent Number: 5,073,644

[45] Date of Patent: Dec. 17, 1991

[54] METHOD OF PREPARING PURE 3-BUTENYL TRIORGANOOXYSILANES, THE INTERMEDIATE PRODUCTS 3,4-DICHLOROBUTYL TRIORGANO-OXYSILANES AND USE OF THE FINAL PRODUCTS

[76] Inventors: Ulrich Deschler, Birkenweg 1; Peter Kleinschmit, Wildaustrasse 19, both of D-6450 Hanau 9; Siegfried Wolff, Weiherstrasse 28, D-5303 Bornheim-Merten; Ewe-Hong Tan, Rembrandtstrasse 22, D-5047 Wesserling, all of Fed. Rep. of Germany

[21] Appl. No.: 375,923

[22] Filed: Jul. 6, 1989

[30] Foreign Application Priority Data

Jul. 11, 1988 [DE] Fed. Rep. of Germany ....... 3823450

[51] Int. Cl.⁵ .................................................. C07F 7/18
[52] U.S. Cl. ..................................... 556/482; 556/485
[58] Field of Search ................................. 556/485, 482

[56] References Cited

U.S. PATENT DOCUMENTS

| 2,512,390 | 6/1951  | Sommer ........................... 556/485 X |
| 2,613,221 | 10/1952 | Ladd et al. ...................... 556/482 X |
| 3,015,585 | 1/1962  | Holbrook et al. ............... 556/485 X |
| 3,310,578 | 3/1967  | Bluestein ......................... 556/485 X |
| 3,536,744 | 10/1970 | Dear .................................. 556/485 |
| 3,696,138 | 10/1972 | Michael et al. .................. 556/485 X |

Primary Examiner—Paul F. Shaver
Attorney, Agent, or Firm—Cushman, Darby & Cushman

[57] ABSTRACT

A method of preparing pure 3-butenyl triorgano oxysilanes, the intermediate products 3,4-dichlorobutyl triorgano oxysilanes and the use of the final products in rubber mixtures reinforced with silicic acid and vulcanizable with peroxides. 3,4-dichlorobutene-1 and trichlorosilane are used as initial products.

4 Claims, 2 Drawing Sheets

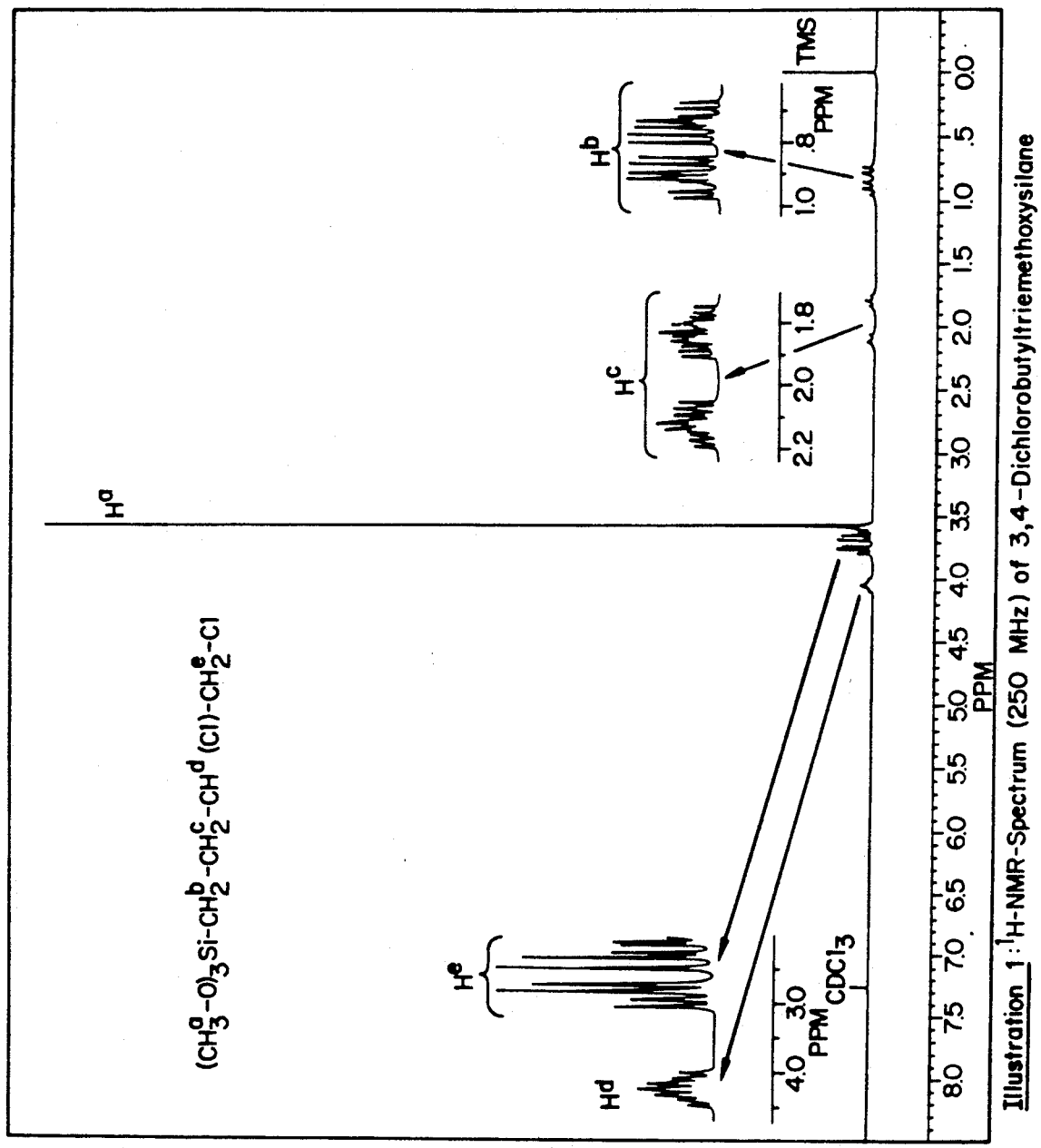
Illustration 1: $^1$H-NMR-Spectrum (250 MHz) of 3,4-Dichlorobutyltriemethoxysilane

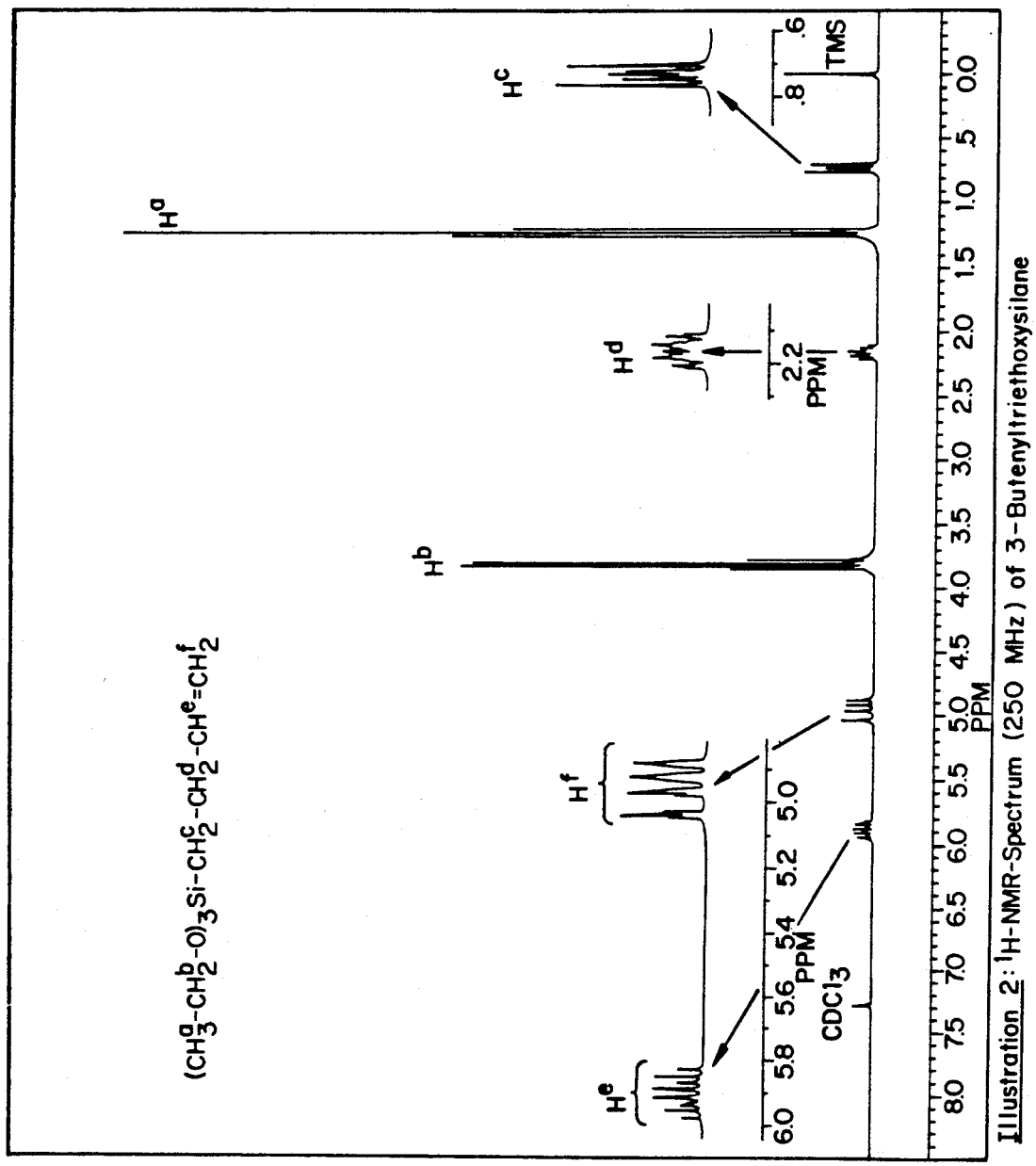
Illustration 2: $^1$H-NMR-Spectrum (250 MHz) of 3-Butenyltriethoxysilane

METHOD OF PREPARING PURE 3-BUTENYL TRIORGANOOXYSILANES, THE INTERMEDIATE PRODUCTS 3,4-DICHLOROBUTYL TRIORGANO-OXYSILANES AND USE OF THE FINAL PRODUCTS

The present invention relates to a method of preparing pure 3-butenyl triorganooxysilanes, the intermediate products 3,4-dichlorobutyl triorganooxysilanes and the use of the final products in rubber mixtures which are reinforced with silicic acid and vulcanizable with peroxides.

BACKGROUND OF THE INVENTION

The preparation of a butenyl triorganooxysilane is described by Capka et al. in Collect. Czech. Chem. Commun. 1976. 41 (4) 1024-9 (C.A. 85:78183m (1976)); however, it is stated that the reaction of $(C_2H_5O)_3SiH$ with 1,3 butadiene does not progress selectively.

The same problem is also discussed in Chemical Abstracts 87:152308r (1977). According to this reference, $(C_2H_5O)_3Si-CH_2-CH_2-CH=CH_2$ is obtained by hydrosilylizing 1,3 butadiene with $(C_2H_5O)_3SiH$. However, this product is obtained in only a very small yield, in addition to two butenyl silanes which are obtained as the main products and are positionally isomeric in relation to the C—C double bond. This is confirmed by Czechoslovakian patent 171,597 of Feb. 15, 1978 (Chemical Abstracts 89:215545e (1978)), which discloses that the compound is suitable for improving the adhesion between organic polymers and inorganic fillers. The use of these compounds in emulsions for the pretreatment of glass fibers is described in Czechoslovakian patent 221,181 B (Chemical Abstracts 105:25289a (1986)) of Mar. 15, 1986. However, this publication does not describe a method of preparation.

E. Lukevics et al., J. Organomet. Chem. Libr., 5 (1977) 26 describe the reaction of trichlorosilane with 1,3-butadiene in which the compound $Cl_3Si-CH_2-CH_2-CH=CH_2$ expected from the 1,2 addition is formed only to a slight degree because of side reactions. These include 1,4 addition with a shifting of the double bond, doubled silylation and telomerization. In addition, there is the risk that the hydrogen chloride released during the reaction will be added to the remaining double bond in a subsequent esterification of the trichlorosilyl function with alcohols to the desired product according to Formula I.

SUMMARY OF THE INVENTION

The object of the present invention therefore is to provide a method for the selective preparation of pure, hydrolyzable, butenyl silanes which have a terminal C—C double bond. Terminal C—C double bonds are expected to provide advantages in the use of the compounds in comparison to centrally located C—C double bonds because of their known, higher reactivity, such as e.g. a more rapid cross-linking by peroxides or a more rapid copolymerization with other monomers. This higher reactivity can be explained by reduced steric hindrance.

The invention provides a method of preparing pure, that is, isomer-free 3-butenyl triorganooxysilanes of the general formula $$(RO)_3-Si-CH_2-CH_2-CH=CH_2 \quad (I)$$

in which R represents $C_1-C_8$ - alkyl, aryl, aralkyl, especially $CH_3$, $C_2H_5$, $C_6H_5$ and $C_6H_5-CH_2-$.

In the method according to the invention:
a) 3,4-dichlorobutene-1 is hydrosilylized with trichlorosilane,
b) The 3,4 dichlorobutyl trichlorosilane produced in step (a) is distilled off,
c) This compound is esterified with an alcohol of the general formula ROH (II) in which R has the significance indicated above,
d) The 3,4-dichlorobutyl triorganooxysilane obtained in the last step is purified by distillation and dehalogenated with sodium metal and
e) The product according to Formula I is isolated.

The hydrosilylization can be carried out in homogeneous or in heterogeneous phase, depending on whether the catalyst is soluble in the reaction medium.

If this step is carried out in a homogeneous phase, the trichlorosilane and the 3,4-dichlorobutene-1 are generally reacted with one another in a molar ratio of 1.0–1.3 to 1 in the presence of a conventional platinum catalyst at temperatures of 25° to 150° C., preferably 35° to 120° C., at atmospheric pressure.

Suitable catalysts for reaction in the homogeneous phase are in particular hexachloroplatinic acid, platinum-(II)-acetyl acetonate or similar platinum compounds known from pertinent survey articles (cf. e.g. E. Lukevics et al., J. Organomet. Chem. Libr. 5 (1977), 3–5) and soluble in organic solvents as well as other suitable catalysts e.g. soluble complexes of the catalytically active transition metals cobalt, nickel, rhodium, palladium or osmium (cf. e.g. J. L. Speier, Adv. Organomet. Chem. 17 (1979), 428).

When heterogeneous catalysts are used, that is, catalysts which are insoluble in the organic medium, a mixture of trichlorosilane and 3,4-dichlorobutene-1, generally in a molar ratio of 1.0–1.3 to 1 in a liquid phase, is conducted at pressures of 1-5 atm through a fixed catalyst bed which can be maintained at a desired temperature by external heating. The residence time of the two reactants in this fixed catalyst bed should be selected so that the reaction to 3,4-dichlorobutyl trichlorosilane is essentially complete after one passage.

Potential catalytically active metals are in particular platinum but also e.g. palladium, rhodium, osmium, cobalt and nickel. Suitable insoluble carriers can be of an inorganic nature (e.g. silica gel, aluminum oxide, activated carbon) or of an organic nature (e.g. polystyrene/divinylbenzene, polymethylmethacrylate/divinylbenzene) (cf. E. Lukevics et al., J. Organomet. Chem. Libr. 5 (1977), pp. 5–6). Platinum-on-activated-carbon catalysts have proved to be especially well-suited as heterogeneous hydrosilylation catalysts on a commercial scale (see, e.g., U.S. Pat. No. 2,637,738; German published patent specification DE-OS 28 15 316).

After the distillation of the reaction mixture obtained in the hydrosilylation, 3,4-dichlorobutyl trichlorosilane precipitates as a colorless, low-viscosity liquid. The trichlorosilyl group is subsequently esterified according to generally known methods with the desired alcohols, especially methanol or ethanol (cf., e.g., Published German Patent Specification DE-OS 20 61 189, British Patent 1,359,312).

3,4-dichlorobutyl triorgano oxysilanes of general Formula III,

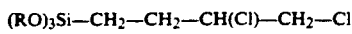

are obtained as intermediate products which can be purified by simple distillation. These are novel products and constitute a part of the subject matter of the present invention.

The last step of the synthesis of the desired compounds of Formula I is dehalogenation of the compounds of Formula III with dissolved or liquefied sodium metal. Sodium chloride is formed as a byproduct.

This reaction is successful both at low temperatures in liquid ammonia and at temperatures of 110° to 140° C. in toluene or xylene as a reaction medium, in almost quantitative yield.

Sodium and dichlorobutyl silanes of general Formula III are used in a molar ratio of 2 to 2.1 to 1. Surprisingly, no side reaction occurs between the sodium metal and the organo oxysilyl groups.

It is immaterial for the success of the reaction whether the organosilane component used (with solvent) is placed in a vessel and liquid sodium introduced or vice versa.

The invention also relates to the use of the compounds prepared in accordance with the invention in vulcanizable rubber mixtures which contain a siliceous filler, optionally in mixtures with carbon black.

It is known that an organosilane must be used in rubber mixtures vulcanizable with peroxide compounds which mixtures should contain a rather large amount of siliceous fillers such as, e.g., precipitated silicic acids, in order to impart sufficiently good properties to the vulcanizates.

Such mixtures according to the state of the art frequently contain vinyl tris (2-methoxyethoxy) silane as the organosilane. However, the breakdown products which are produced from this silane during the preparation/vulcanization of the mixture have been considered to be toxicologically hazardous.

According to the present invention, these rubber mixtures now contain, instead, at least one compound of the general Formula I

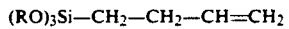

in an amount of 0.2-15 parts per hundred parts by weight of rubber(phr), preferably 0.2-6 phr.

The other constituents of vulcanizable rubber mixtures are known to persons skilled in the art.

The rubbers which are useful for this purpose include, individually or in a mixture with each other, e.g., natural and synthetic rubbers, which can be oil-extended, such as butadiene rubbers, isoprene rubbers, butadiene-styrene rubbers, butadiene-acrylonitrile rubbers, terpolymers of ethylene, propylene and non-conjugated dienes, hydrated acrylonitrile rubbers and chlorosulfonated polyethylene. Rubber blends of the named rubber types with other polymers in lesser amounts can also be used according to the invention.

The siliceous fillers which can be used according to the invention, which can be used alone or in mixtures of such fillers, are known in the rubber art. The concept "siliceous filler" is a broad one which refers to fillers which are compatible with rubbers, compatible in rubbers or which can be worked into rubber mixtures, which fillers consist of silicates, contain silicates and/or contain silicates chemically bound in the broadest sense.

The following in particular are included among the siliceous fillers:

Highly disperse silicic acid fillers (silicon dioxide) with specific surfaces (BET surface measured with $N_2$) in a range of approximately 5 to 300, preferably 5 to 250 $m^2/g$ and with primary particle sizes in a rang of approximately 10 to 400 nm which can be prepared e.g. by precipitation from solutions of silicates with inorganic acids, by hydrothermal digestion, by hydrolytic and/or oxidative high-temperature reaction of volatile silicon halogenides or by an arc method. These silicic acids can optionally also be present as mixed oxides or oxide mixtures with the oxides of the metals aluminum, magnesium, calcium, barium, zinc, zirconium and/or titanium.

Synthetic silicates, e.g. aluminum silicate or alkaline-earth silicates such as magnesium silicate or calcium silicate with specific surfaces of approximately 20 to 300 $m^2/g$ and primary particle sizes of approximately 10 to 400 nm.

Natural silicates, e.g. kaolines, argils, clays as well as natural silicic acids such as e.g. quartz and kieselguhr.

Glass fibers and glass-fiber products such as mats, strands, fabrics, place mats and the like as well as microglass balls.

The following can be cited as useful filler mixtures: silicic acid/kaoline or silicic acid/glass fibers/asbestos as well as blends of silicate-containing reinforcing fillers with the known rubber carbon blacks, e.g. silicic acid-/ISAF carbon black or silicic acid/glass fiber cord-/HAF carbon black.

Carbon black can also be present in the rubber mixtures of the invention, not only for coloring the vulcanizates ray or black but also for achieving special, valuable vulcanizate properties. The known rubber carbon blacks are preferred for this. The carbon black is used in the rubber mixtures of the invention in amounts of up to 150 parts by weight, preferably from 0.1 to 80 parts by weight, relative to 100 parts by weight of rubber.

For the case in which siliceous filler and carbon black are present in the rubber mixtures, the total filler content is limited to a maximum of 400 parts by weight, relative to 100 parts rubber. In the of more active silicic-acid fillers, 150 parts by weight can be considered as the upper limit.

It can also be especially advantageous if the rubber mixtures contain softeners or softener oils, e.g. paraffinic softener oils. The amount of softener oil can vary within broad limits; thus, it can be more than 0.5 or 5 parts by weight, especially more than 10 to approximately 100 parts by weight.

Moreover, oxides of polyvalent metals like those also used in the rubber art can be added in amounts of 1-10 parts by weight, relative to 100 parts by weight of the rubber. The metal oxides include first and foremost zinc oxide, especially in a finely divided form.

The peroxides used in the rubber-processing industry are suitable as cross-linking agents. The utilizable peroxides include e.g. benzoyl peroxide, 1,3 bis (tert. butyl-peroxy-isopropyl) benzene, p-chlorobenzoyl peroxide, tert. butylcumyl peroxide, di-tert. butyl peroxide, dicumyl peroxide and 2,5-dimethyl 3,5-(di-tert. butyl peroxy) hexane.

The rubber mixtures according to the invention are prepared in the following manner. A two-stage mixing cycle is preferred. In the first mixing stage, the following constituents are mixed in a kneader at flowthrough temperatures between 55° and 60° C.: Rubber, siliceous filler, the silane of the present invention, softener oil, zinc oxide and all other chemicals except for peroxides filled with a heterogeneous platinum contact and with a volume of 750 mm at a jacket temperature of 65° C.

TABLE 1

Selected Composition and Analytical Data for the Described Silanes

| Designation | Chemical Composition | Empirical Formula | Molecular Weight | Appearance | Boiling Point [°C./mm] |
|---|---|---|---|---|---|
| 3,4-Dichlorobutyl-trichlorosilane | $Cl_3Si-CH_2-CH_2-CH(Cl)-CH_2-Cl$ | $C_4H_7Cl_5Si$ | 260.45 | Colorless liquid | 84/3 [5]* |
| 3,4-Dichlorobutyl-trimethoxysilane | $(CH_3O)_3Si-CH_2-CH_2CH-(Cl)-CH-Cl$ | $C_7H_{16}Cl_2O_3Si$ | 247.19 | Colorless liquid | 71/0.3 |
| 3,4-Dichlorobutyl-triethoxysilane | $(C_2H_5O)_3Si-CH_2-CH_2-CH(Cl)-CH-Cl$ | $C_{10}H_{22}Cl_2O_3Si$ | 289.28 | Colorless liquid | 90/0.6 |
| 3-Butenyl-trimethoxysilane | $(CH_3O)_3Si-CH_2-CH_2-CH=CH$ | $C_7H_{16}O_3Si$ | 176.29 | Colorless liquid | 56/15 |
| 3-Butenyltriethoxysilane | $(C_2H_5O)_3Si-CH_2-CH_2-CH=CH$ | $C_{10}H_{22}O_3Si$ | 218.37 | Colorless liquid | 64/6 |

| Designation | Density (g/cm³) | | Elementary Analysis | | | |
|---|---|---|---|---|---|---|
| | | | C (%) | H (%) | Cl (%) | SiO₂ |
| 3,4-Dichlorobutyl-trichlorosilane | — | calculated: | 18.45 | 2.91 | 68.06 | 23.07 |
| | | found: | — | — | — | — |
| 3,4-Dichlorobutyl-trimethoxysilane | 1.17 | | 34.01 | 6.52 | 28.68 | 23.7 |
| | | | 34.6 | 6.4 | 28.2 | 23.7 |
| 3,4-Dichlorobutyl-triethoxysilane | 1.08 | | 41.52 | 7.67 | 24.51 | 20.77 |
| | | | 41.2 | 7.9 | 23.8 | 20.2 |
| 3-Butenyl-trimethoxysilane | 0.95 | | 47.69 | 9.15 | — | 34.08 |
| | | | 48.2 | 9.0 | — | — |
| 3-Butenyltriethoxysilane | 0.90 | | 55.00 | 10.15 | — | 27.51 |
| | | | 55.7 | 10.16 | — | — |

*M. A. Mamedor et al., Zh. Obshch. Khim. 35, 461; CA 63, 626 g (1965)

in the first minute; after a total of 4 minutes, the mixture is removed from the kneader.

In the second mixing stage, the peroxide is added to the premix from the first mixing stage now on the roller at a flowthrough temperature of approximately 15° C.

This two-stage mixing method avoids a premature scorching of the mixture. Industrial areas of application for the described rubber mixtures and their vulcanizates are. e.g.: Industrial rubber articles such a cable jackets, hoses, heating hoses, roller coverings, electric insulations, seals, injection profiles and jacketings.

DETAILED DESCRIPTION OF PREFERRED EMBODIMENTS

The invention is illustrated by the following examples. In these examples, all reactions are carried out in standard laboratory apparatus consisting of glass vessels under an atmosphere of nitrogen.

EXAMPLE 1

3,4-dichlorobutyl trichlorosilane,
$Cl_3Si-CH_2-CH_2-CH(Cl)-CH_2-Cl$ a) Preparation over homogeneous Pt catalyst 596 g trichlorosilane (4.4 moles, excess) and 500 g 3,4-dichlorobutene-1 (4 moles) are mixed. 0.4 g Pt(II)-acetyl acetonate are added to 30 ml of this mixture, at which time the temperature gradually rises by itself to 95° C. At this temperature, the remaining trichlorosilane/olefin mixture is added and allowed to react for an additional half hour at 92° C. Excess trichlorosilane and other readily volatile constituents are drawn off in a vacuum. The crude product obtained in this manner (826 g≈79.3% of theory) is subsequently purified by distillation. 705 g 3,4-dichlorobutyl trichlorosilane 67.7% of theory are obtained as the main fraction (see table 1 for composition data).

b) Preparation over a heterogeneous Pt catalyst 286 ml (1.37 moles/hour) of a precisely stoichiometric mixture of 3,4-dichlorobutene-1 and trichlorosilane per hour are fed into a double-jacketed flow reactor filled with a heterogeneous platinum contact and with a volume of 750 mm at a jacket temperature of 65° C.

After 3.5 hours operating time, 1239.4 g liquid product mixture (=99.3% of the expected amount) are obtained. The following composition can be derived from the ¹H-NMR spectrum of this product mixture:

| 86 molar % = | 91.5% by weight | 3,4-dichlorobutyl trichlorosilane |
| 9 molar % = | 4.6% by weight | 3,4-dichlorobutene-1 |
| 5 molar % = | 3.9% by weight | n-butyl trichlorosilane |

EXAMPLE 2

3,4-dichlorobutyl trialkoxysilanes,
$(RO)_3Si-CH_2-CH_2-CH(Cl)-CH_2-Cl$ a) Esterification with methanol 1264.4 g 3,4-dichlorobutyl trichlorosilane (4.85 moles) are combined in the course of 4 hours at 20° to 30° C. with 513.3 g methanol (16 moles, excess) while nitrogen is vigorously passed through the reaction mixture for a more rapid removal of HCl. Then, the mixture is heated and agitated for 2 hours at approximately 75° C. 1142 g crude product (=95.3% of theory) is obtained after the reaction mixture has cooled off, from which raw product 1072 g (89.4% of theory) purified product can be obtained by distillation (substance data cf. table 1, ¹H-NMR spectrum see FIG. 1).

b) Esterification with ethanol 877.1 g (=97.5% of theory) raw silane and 803.7 g=89.4% of theory distillatively purified silane are obtained in an analogous manner from 809.6 g 3,4-dichlorobutyl silane (3.1 moles) and 472.5 ethanol (10.3 moles, excess).

EXAMPLE 3

3-butenyl trialkoxysilanes,
$(RO)_3Si-CH_2-CH_2-CH=CH_2$ a) Dechlorination with sodium in liquid ammonia 23 g sodium (1 mole) are placed in a 500 ml flask and approximately 150 ml ammonia condensed in at −70° C. 123.6 g 3,4-dichlorobutyl trimethoxysilane (0.5 mole) is added dropwise to the deep-blue solution produced in the course of 1 hour at −55° C. while the reaction mixture visibly changes color. The ammonia is allowed to evaporate overnight from the colorless, highly viscous suspension produced, the colorless residue combined with 150 ml n-pentane, the NaCl (56.9 g≈97.5% of theory) removed by filtration and 88.2 of a colorless liquid corresponding to the expected amount is obtained after the solvent is drawn off. 75.7 g=85.9% of theory of pure 3-butenyl trimethoxysilane are obtained therefrom by distillation (cf. table 1).

b) Dechlorination with sodium in xylene 115.0 g sodium (5 moles) and 1000 ml xylene are heated under vigorous agitation to 135° C. so that a sodium emulsion develops. 723.2 g 3,4-dichlorobutyl triethoxysilane (2.5 moles) are added thereto at this temperature within 2.5 hours. After a reaction time of 2 hours at 13° C., the precipitated NaCl (290 g≈99.3% of theory) is filtered off and the solvent drawn off. The raw product (524.8 g≈96% of theory) is purified by distillation. The main fraction thereof with 437.8 g≈80.2% of theory is the desired product (cf. table 1, $^1$H-NMR spectrum see FIG. 2).

c) Dechlorination with sodium in boiling toluene

A mixture of 578.6 g 3,4-dichlorobutyl triethoxysilane (2.0 moles) and 750 ml toluene is combined at reflux temperature within 2 hours with 92.0 g molten sodium in a heatable (approximately 130° C.) dropping funnel. In order to complete the reaction, the mixture is subsequently agitated for 30 minutes more at 120° C. After the workup already described in b), 417.3 g crude product=95.4% of theory are obtained which yield 366.0 g 3-butenyl triethoxysilane as a main fraction in the subsequent vacuum fractionation, corresponding to 83.7% of theory.

EXAMPLE 4

The following is an example of a formulation for the rubber mixtures of the present invention, together with test results.

The physical tests are carried out at room temperature in accordance with the following standard specifications:

Tensile strength
(Tensile) modulus 100%:
(Tensile) modulus 200%:
(Tensile) modulus 300%: DIN 53 404 measured in MPa
Breaking elongation: DIN 53 404 measured in %
DIN abrasion: DIN 53 516 measured in (mm$^3$)
Compression set: ASTM D 395, method B measured in %.

The following names and abbreviations are used in the example of rubber formulations, the meanings of which are indicated in the following.
Keltan 712: terpolymer consisting of ethylene, propylene and dienes (DSM, Holland)
Ultrasil ®
VN 3 Gran.: fine, precipitated silicic acids, BET surface 175 m$^2$/g (Degussa)
Circosol 4240: softener oil (Sun Refining and Marketing Co.)
Perkadox 14/40:1,3-bis-(tert.butyl-peroxy-isopropyl) benzene (AKZO)

|  | 1 | 2 | 3 |
|---|---|---|---|
| Keltan 712 | 100 | 100 | 100 |
| Ultrasil VN 3 Gran. | 40 | 40 | 40 |
| Circosol 4240 | 10 | 10 | 10 |
| zinc oxide RS | 5 | 5 | 5 |
| 3-butenyl trimethoxysilane | — | 0.6 | 1.2 |
| Perkadox 14/40 | 6.5 | 6.5 | 6.5 |
| vulcanization: 50 min. at 160° C. tensile strength (MPa) | 13.0 | 11.0 | 9.8 |
| (tensile) modulus 100% (MPa) | 1.7 | 2.2 | 2.4 |
| (tensile) modulus 200% (MPa) | 3.0 | 4.8 | 5.7 |
| (tensile) modulus 300% (MPa) | 4.8 | 9.3 | — |
| breaking elongation (%) | 510 | 330 | 270 |
| DIN abrasion (mm$^3$) | 166 | 122 | 113 |
| compression set B (%) 22 h/70° C. | 14.9 | 11.6 | 9.8 |

This example shows that the use of the 3-butenyl trimethoxysilane of the invention greatly improves the (tensile) moduli. In addition, abrasion and compression set are significantly reduced, which is advantageous for industrial articles.

What is claimed is:

1. A method of preparing pure 3-butenyl triorgano oxysilanes of the Formula I:

$$(RO)_3-Si-CH_2-CH_2-CH=CH_2 \qquad (I)$$

in which

R represents a member of the group consisting of C$_1$–C$_8$-alkyl, aryl and aralkyl said method comprising:
   a) hydrosilylating 3,4-dichlorobutene-1 with trichlorosilane and distilling off the 3,4 dichlorobutyl trichlorosilane thereby produced,
   b) Esterifying the compound produced in step a) with an alcohol of the general formula ROH (II) in which R has the significance indicated above,
   c) dehalogenating the 3,4-dichlorobutyl triorgano oxysilane obtained in step b) with sodium metal and
   d) isolating the product according to Formula I.

2. A process as set forth in claim 1 in which R is selected from the group consisting of CH$_3$, C$_2$H$_5$, C$_6$H$_5$ and C$_6$H$_5$—CH$_2$—.

3. 3,4-dichlorobutyl triorgano oxysilanes of the Formula III $$(RO)_3Si-CH_2-CH_2-ClCH-ClCH_2 \qquad (III)$$

in which R represents a member of the group consisting of C$_1$–C$_8$-alkyl, aryl and aralkyl.

4. 3,4-dichlorobutyl triorgano oxysilanes as set forth in claim 3 in which R is selected from the group consisting of CH$_3$, C$_2$H$_5$, C$_6$H$_5$ and C$_6$H$_5$—CH$_2$—.

* * * * *